United States Patent [19]
Ekström

[11] Patent Number: 5,971,937
[45] Date of Patent: Oct. 26, 1999

[54] BLOOD ALCOHOL CONCENTRATION MEASURING FROM RESPIRATORY AIR

[75] Inventor: Jan Petri Ekström, Helsinki, Finland

[73] Assignee: Instrumentarium Oy, Helsinki, Finland

[21] Appl. No.: 08/670,811

[22] Filed: Jun. 25, 1996

[30] Foreign Application Priority Data

Jun. 26, 1995 [FI] Finland ..................................... 953166

[51] Int. Cl.⁶ ........................................................ A61B 5/00
[52] U.S. Cl. .............................. 600/532; 422/84; 73/23.3; 600/543
[58] Field of Search .................................... 128/719, 716, 128/730; 422/84; 73/23.3; 180/272

[56] References Cited

U.S. PATENT DOCUMENTS

| | | | |
|---|---|---|---|
| 3,823,601 | 7/1974 | Hopesch ..................................... | 422/84 |
| 3,830,630 | 8/1974 | Kiefer et al. . | |
| 4,090,078 | 5/1978 | Heim . | |
| 4,316,380 | 2/1982 | Heim et al. ............................... | 128/719 |
| 4,459,994 | 7/1984 | Slemeyer ................................. | 128/719 |
| 4,649,027 | 3/1987 | Talbot . | |
| 4,736,619 | 4/1988 | Legrand . | |
| 4,809,810 | 3/1989 | Elfman et al. . | |
| 5,274,550 | 12/1993 | Greenlee . | |
| 5,376,555 | 12/1994 | Forrester et al. . | |

FOREIGN PATENT DOCUMENTS

| | | |
|---|---|---|
| 28 36 886 | 3/1980 | Germany . |
| 29 28 433 | 1/1981 | Germany . |
| WO 92/22813 | 12/1992 | WIPO . |

OTHER PUBLICATIONS

*Mastering Infra–red Capnography*, Z. Kalenda, M.D., Meritus Professor of Neuro–Anaesthesiology, University of Utrecht, the Netherlands, pp. 38–41 and 104–105, 1989.

*Primary Examiner*—Robert L. Nasser
*Attorney, Agent, or Firm*—Andrus, Sceales, Starke & Sawall

[57] ABSTRACT

A method and apparatus for measuring a blood alcohol content value by means of a breath alcohol concentration as well as for securing the reliability of this measured value. The apparatus comprises: sensor elements (1) for obtaining a measured alcohol concentration value from an incoming exhalation air stream; sensor elements (1) for obtaining a measured carbon dioxide concentration value from the same exhalation air stream (9); as well as first output elements (2) for producing, if necessary, a result proportional at least to a blood alcohol content. The apparatus further includes a first memory (M1) for storing a predetermined carbon dioxide lower threshold value or lower threshold values (R1, R2, R3 and/or Rf) and/or an upper threshold value or upper threshold values (R4, R5, R6 and/or Rg) and a first comparing element (C1) for comparing the measured carbon dioxide concentration value to said threshold values as well as a first logic element (L1) for producing outputs of a preset type depending on whether the measured carbon dioxide concentration fails to reach or exceeds the predetermined lower threshold values or upper threshold values.

65 Claims, 3 Drawing Sheets

BLOOD ALCOHOL CONCENTRATION MEASURING FROM RESPIRATORY AIR

BACKGROUND OF THE INVENTION

The present invention relates to a method for confirming the reliability of a blood alcohol concentration value to be measured from respiratory air. In this method, the incoming exhalation air is sampled during exhalation, for at least one measured alcohol concentration value and, during the same respiratory stage, it is sampled for at least one measured carbon dioxide concentration value. A result is produced which is proportional to the blood alcohol concentration value and which is based on one or more measured alcohol concentration values obtained during exhalation from the lungs.

The invention relates also to an apparatus for implementing such measurement, said apparatus comprising sensor elements for obtaining a measured alcohol concentration and carbon dioxide concentration value from the incoming exhalation air stream as well as output elements for producing, if necessary, a result which is proportional at least to the blood alcohol concentration.

For quite some time, the detection of blood alcohol content has been effected by means of testing devices which measure the air stream exhaled by a subject for its alcohol concentration which, as known, is to a certain degree proportional to the blood alcohol content, provided that the measured exhalation air originates in the deep lungs, and thus consists of so-called alveolar gases. Hence, the measurements are based on the hypothesis that a given alcohol concentration value measured from exhalation air always corresponds to a given blood alcohol concentration value. However, an effort to determine blood alcohol concentration by means of the alcohol concentration in exhalation air involves several sources of error. The publication DE 2,928,433 pursues a solution to the problem that the alcohol concentration of exhalation air fluctuates in time with the heart rate, which of course is not the case with the concentration of blood alcohol. As a solution to this problem, the cited publication discloses a control device capable of logical functions and calculation. On the other hand, the publication U.S. Pat. No. 5,376,555 describes an arrangement for eliminating the effect of possible, so-called mouth alcohol at the initial stage of sampling the respiratory air. The fact is, namely, that if alcohol has been ingested just prior to measuring, the alcohol contained in the mouth as a result thereof produces a relatively high concentration peak in the alcohol content measured at the start of a breath sample. The effect of this peak is eliminated as described in the cited publication by making use of the carbon dioxide concentration also measured at the early stage of exhalation. If this is not done, the result may be a high breath alcohol concentration and, on the basis of presumed correlation, a too high estimate for blood alcohol content that does not correspond to true blood alcohol content. Thus, an object of the cited publication is to eliminate the incorrectly excessive alcohol concentration caused by mouth alcohol.

In addition to the above sources of error, there are other sources of error which produce too low an alcohol concentration measure with respect to true blood alcohol content. For example, if a subject takes a few or several very deep breaths to create a hyperventilation prior to measuring alcohol concentration from alveolar air, the alcohol concentration measure obtained thereafter will be lower than it would be had the subject breathed in a normal manner. As a result of this, the estimate of blood alcohol content made on the basis of the measured value is also too low. This is the case even if the air exhaled by a subject in actual alcohol measuring has a sufficient volume and comes from the deep lungs in a proper manner and, thus, consists of alveolar gases. This hyperventilation has been described e.g. in the book Z. Kalenda: MASTERING INFRARED CAPNOGRAPHY, 1989.

An incorrect result is also obtained if a subject, during measuring, restricts the amount and/or duration of his or her exhalation. Also in this case the measured alcohol concentration will be lower than what it would be had the subject exhaled from the deep lungs in a normal manner and also the estimate of blood alcohol content made on the basis of the measured value will be too low.

A solution to this latter problem has been pursued e.g. by training the measuring device operating personnel, whereby the measuring device operator aims to oversee that a subject being examined exhales properly into the measuring device. However, this procedure is highly unreliable and different persons have substantially different pulmonary capacities and, thus, there are no guarantees regarding a sufficient exhalation time and/or exhalation volume.

There are also situations which can produce an excessive measured alcohol concentration value. Such a situation is for example hypoventilation which is a reverse situation to the above hyperventilation and in which a subject breaths less than normal. In a hypoventilation situation, the $CO_2$ concentration and alcohol concentration of an alveolar gas are higher than which would be the values correctly corresponding to the concentrations in blood. Thus, the alcohol concentration determined from an alveolar gas in a hypoventilation situation is higher than the equilibrium alcohol content of the human body and blood. In hypoventilation, a subject can be falsely convicted of intoxicated driving if the hypoventilation is not detected.

The publication U.S. Pat. No. 3,830,630 discloses a system, wherein a resistance bridge consisting of filaments is used for measuring both $CO_2$-content and alcohol content from exhalation air. These two content measurements are linked to each other such that, if the measured carbon dioxide content rises to a minimum value of 4.5%, the resulting alcohol measurement is found to be correct. The cited publication states further that the $CO_2$-content and alcohol content are in equilibrium with blood alcohol content when the carbon dioxide content is 5%–5.25%. As for the above-described error situations, this prior art system only eliminates those caused by hyperventilation and even that requires that it indeed be alveolar exhalation air which is being measured. The publication mentions nothing about the necessity of monitoring this, nor does it describe any means for securing this aspect. This system may cause further errors for the reason that various persons have individual differences in the carbon dioxide concentration of a normal alveolar gas, the fluctuation range being roughly 4.7%–5.5%. If, for example, the normal alveolar $CO_2$-content of a person is 5.5% and the person blows into an alcohol measuring device and stops exhalation before the exhalation air comes from the sufficiently deep lungs, the exhalation may have a maximum $CO_2$-content of for example 4.6%. According to the cited publication, this result is acceptable. As a matter of fact, the alcohol content measured from this particular exhalation is too low.

SUMMARY OF THE INVENTION

Hence, an object of the invention is to provide a method and an apparatus, whereby it is possible to make sure that the alcohol concentration measured from exhalation air is as correct as possible and thus in a per se known manner as proportional as possible to the blood alcohol content of a subject being examined. A particular parallel object of the invention is to make sure that a subject being examined does not have a chance to exert a lowering effect on the measured alcohol concentration value by taking a few or several deep breaths prior to measuring and/or by restricting the duration and/or volume of his or her exhalation during measuring, i.e. by using hyperventilation. Likewise, a particular second parallel object of the invention is to try and prevent a subject being examined from involuntarily acting to increase the measured alcohol concentration value by restricting the duration and/or volume of his or her exhalation prior to measuring, i.e. from ending up in hypoventilation. A third object of the invention is to try and eliminate the effect of differences in carbon dioxide concentrations found in exhalation air between individuals on the measured result and its reliability. A fourth object of the invention is to provide the operator of an alcohol concentration measuring device with a clear indication about the reliability of each individual measurement and whether other, and which, further measures are needed. Thus, the object is to replace some of the supervision required of a measuring device operator with precise and exact information produced on the basis of the data measured by the measuring apparatus itself.

The above-described drawbacks can be eliminated and the above-defined objects can be achieved by means of a method of the invention, which is characterized by what is defined in the claims and by means of an apparatus of the invention, which is characterized by what is defined in the claims.

The most important benefit of the invention is that, when applying a method and using an apparatus in accordance therewith for measuring alcohol concentration from the exhalation air stream of a subject, it is clearly and reliably verifiable whether or not the measured alcohol concentration value is perfectly applicable or possibly whether or not the measured value is applicable to some extent. Thus, by means of the invention it is possible to verify or confirm the reliability of the level of blood alcohol content determined by means of the concentration of breath alcohol. In addition, when proceeding according to the invention, it is possible to detect whether a subject being examined affects intentionally and/or unintentionally the measuring result. Furthermore, in the most preferred embodiments, it is possible to make sure that the final measured values are obtained from real alveolar breath and the effects of differences in individual carbon dioxide concentrations existing in exhalation air can be eliminated.

BRIEF DESCRIPTION OF THE DRAWING

The invention will now be described in more detail with reference made to the accompanying drawings.

DETAILED DESCRIPTION OF THE PREFERRED EMBODIMENTS

In a method as defined by the invention, the exhalation air of a subject is first measured for its alcohol concentration either continuously or periodically by using some prior known method, such as infra-red absorption, as explained hereinbelow in reference to an apparatus. In addition to this and according to the invention, the exhalation air of a subject is measured for its carbon dioxide concentration either continuously or periodically in some prior known manner, such as infra-red absorption, explained hereinbelow in reference to an apparatus.

Thus, from the exhalation air is extracted at least one measured alcohol concentration value Ra and during the same respiratory cycle at least one measured carbon dioxide concentration value Rb. In the context of this invention, the same respiratory cycle means that between each measurement of alcohol concentration and each measurement of carbon dioxide concentration there is a time difference Td which is small in relation to a total exhalation time Tm or the time difference Td is zero, i.e. there is no time difference at all. The asterisks shown in FIG. 3B represent certain possible, periodically effected, separate alcohol and carbon dioxide concentration measurements. On the other hand, the graphs shown in the figures represent results from continuously effected measurements. Generally speaking this indicates that, if the alcohol concentration Ra is measured for example over an initial stage F1 or a rising stage F2 of exhalation, the carbon dioxide concentration must also be measured over the initial stage F1 or rising stage F2 of exhalation, this being the procedure in the cited publication U.S. Pat. No. 5,376,555 for detecting mouth alcohol.

Figure 3A:
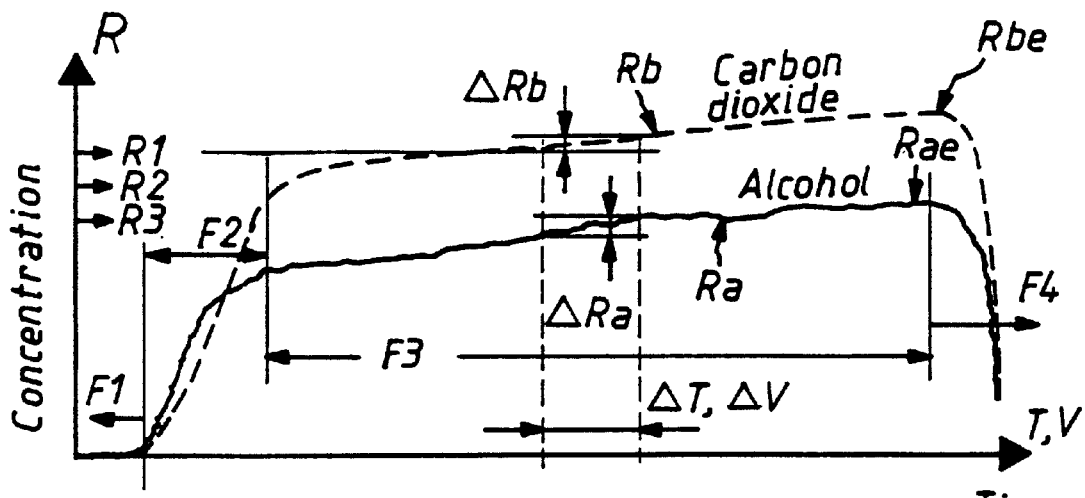
FIG. 3A illustrates alcohol and carbon dioxide concentration values found in the exhalation air stream as a subject exhales normally from the deep lungs and has not made an attempt to decrease the measured alcohol concentration result.
Figure 3B:
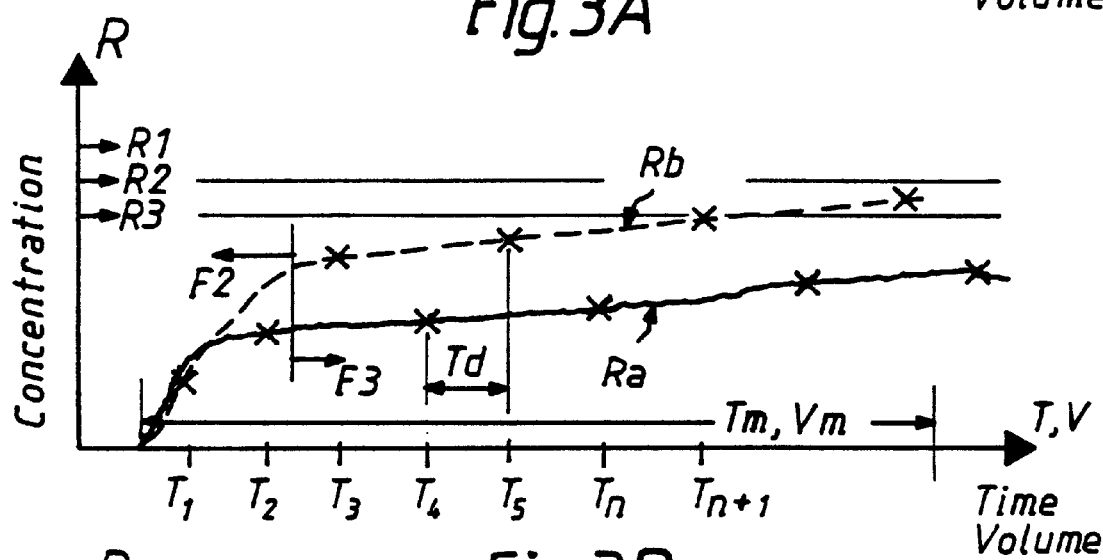
FIG. 3B illustrates alcohol and carbon dioxide concentration values detected in the exhalation air stream in the case that a subject has taken several deep breaths prior to measuring and exhales normally from the deep lungs during measuring, the blood alcohol level being the same as in the case of FIG. 3A.

Generally, the exhalation air stream comprises sequences or stages F1–F4 illustrated in FIG. 3A. Right at the beginning of exhalation there is an initial stage F1, the air representative thereof coming from an anatomically inactive part of the body, in other words, from the mouth and upper respiratory tracts, as well as including a "dead" gas which comes from the initial volume of a measuring apparatus and in which the proportion of air coming from the lungs increases as exhalation continues. This is followed by a plateau stage F3, wherein the gas comprises nothing but a deep lung, so-called alveolar gas. At the end of this stage there is obtained an end-tidal measuring value. Over a final stage F4, the concentration values fall down rapidly.

According to the present invention, the measuring is effected on alcohol concentrations and carbon dioxide concentrations occurring particularly in the latter stage of exhalation, the measuring of both of these being targeted at the deep lung, so-called alveolar exhalation gas, which occurs or should occur over the plateau stage F3 of alcohol concentration and the detected carbon dioxide concentration. Thus, the invention is based on the unexpected discovery that, unlike in the beginning of exhalation, there is a parallel correlation between alcohol concentration Ra and carbon dioxide concentration Rb at the later stage of exhalation. In order that the alcohol concentration measured from alveolar air be as highly representative as possible of the real blood alcohol content, the output is produced by using the breath alcohol concentration measured at quite a late stage of exhalation for obtaining it as surely as possible from the deep lung alveolar gas.

According to the invention, the carbon dioxide concentration of exhalation air is also measured for an output from an essentially equally late stage of exhalation in order to obtain also the carbon dioxide content as surely as possible from the deep lung alveolar gas.

Normally, it is desirable to measure both concentrations over the plateau stage F3 of exhalation, provided that one exists in the exhalation. In order to make use of this phenomenon in a measuring of the invention, the measurement of alcohol concentration and that of carbon dioxide concentration are carried out over the same exhalation stage F3 and typically the time difference Td between each alcohol concentration measurement and a corresponding carbon dioxide concentration measurement is no more than 30% of the total exhalation time Tm. The smaller the time difference Td between the alcohol concentration measurement and the carbon dioxide concentration measurement, the more reliably these concentrations have been measured during the same respiratory stage. If carbon dioxide and alcohol are both measured continuously, the time difference Td is very small.

According to the invention, if one or more carbon dioxide concentration values measured from exhalation air stream or all measured values Rb are lower than a predetermined lower threshold value R1 and/or R2 and/or R3 and/or Rf, special actions are taken for delivering this information in a suitable form to the operator. In exactly the same way, according to a second principle of the invention, if one or more values of carbon dioxide concentration measured from an exhalation air stream or all measured values Rb are higher than a predetermined upper threshold value R4 and/or R5 and/or R6 and/or Rg, special actions are taken to deliver this information in a suitable form to the operator. Normally, when a person exhales and especially when he or she exhales from the deep lungs, i.e. an alveolar gas, the latter has a carbon dioxide concentration which is quite accurately within the range of 4.7–5.5% $CO_2$. Generally, the exhalation air coming from the lungs has a carbon dioxide concentration value which is close to 5% $CO_2$. In case the air exhaled by a person has a $CO_2$ concentration which departs from the range of 4.7–5.5%, there is some special reason for this, as explained in the work Z. Kalenda: MASTERING INFRA-RED CAPNOGRAPHY, 1989.

FIG. 3A illustrates carbon dioxide and alcohol concentrations appearing in normal exhalation coming from the deep lungs, wherein the passages of concentration graphs Ra and Rb over a plateau stage F3 represent alveolar concentrations. Thus, the carbon dioxide concentration Rb has a final value Rbe which rises roughly to the value of 5% $CO_2$, the alcohol concentration having a corresponding final value Rae (a so-called end-tidal value) which is correct and good for disclosing a value proportional to the blood alcohol content or a blood alcohol concentration value calculated therefrom. Thus, the resulting blood alcohol content value is highly equivalent to the true value.

FIG. 3A also includes possible carbon dioxide concentration lower threshold values R1–R3, whereby a carbon dioxide concentration value above the uppermost R1 thereof indicates the usefulness of an exhalation and, as far as the latter is concerned, a possibility of producing a useful alcohol concentration value. This application employs graded lower threshold values R1, R2 and R3 but it is possible to employ just a single lower threshold value R1 or two lower threshold values R1 and R2 or possibly a larger number of lower threshold values than the above three or a variable lower threshold value Rf to be described hereinbelow.

According to the invention, the lower threshold values are generally set lower than or equal to 4.7% $CO_2$, although it is conceivable to set some lower threshold value within the range of 4.5–5.0% $CO_2$. Thus, a single employed lower threshold value R1 can be set e.g. within the range of 4–4.7% $CO_2$ or within the range of 3.5–4% $CO_2$ or at a value lower than this, depending on the desired accuracy and reliability of the result. In case two lower threshold values R1 and R2 are employed, the former can be set e.g. within the range of 4–4.7% $CO_2$ and the other within the range of 3.5–4% $CO_2$ or R1 can be set within the range of 3.5–4.7% $CO_2$ and R2 at a value lower than 3.5% $CO_2$. If three lower threshold values R1, R2 and R3 are employed, these can be set e.g. within the ranges of 4–5.5% $CO_2$, 3.5–4% $CO_2$ and 3.0–3.5% $CO_2$, respectively, or in some other manner. The variable lower threshold value Rf, or a function resulting in variable lower threshold values, is designed such that the above principles are carried out.

In a similar manner, FIG. 3C also includes possible upper threshold values R4–R6 for carbon dioxide concentration, the carbon dioxide concentration value setting below the lowermost R4 of these indicating the acceptability of exhalation and, in that respect, a possibility of obtaining a useful alcohol concentration value. This situation involves the use of graded upper threshold values R4, R5 and R6 but it is possible to employ just one upper threshold value R4 or two upper threshold values R4 and R5 or possibly more numerous upper threshold values than said three or a variable upper threshold value Rg to be described hereinbelow.

According to the invention, the upper threshold values are generally set to be higher than or equal to 5.5% $CO_2$, although it is conceivable to set some upper threshold value within the range of 5.3–6.0% $CO_2$. Thus, one employed upper threshold value R4 can be set e.g. within the range of 5.5–6% $CO_2$ or within the range of 6–6.5% $CO_2$ or at a value higher than this, depending on the desired accuracy and reliability of the result. In case two upper threshold values R4 and R5 are used, the first can be set e.g. within the range of 5.5–6% $CO_2$ and the second within the range of 6–6.5% $CO_2$ or R4 can be set within the range of 6–6.5% $CO_2$ and R5 at a value higher than 6.5% $CO_2$. If three upper threshold values R4, R5 and R6 are employed, these can be set e.g. within the range of 5.5–6% $CO_2$, 6–6.5% $CO_2$ and 6.5–7% $CO_2$ or in some other way. A function producing the variable upper threshold value Rg or variable upper threshold values is designed so as to fulfill the above-described principles.

The previous paragraph has mainly dealt with fixed predetermined threshold values but, according to the invention, it is also possible to employ a predetermined variable threshold value or threshold values Rf and/or Rg. Such a variable threshold value Rf and Rg is determined in accordance with some predetermined function separately at each measurement on the basis of carbon dioxide concentration and/or alcohol concentration measuring results yielded by that particular measurement. Hence, the threshold value Rf is a continuous function and different for each measurement but, as the function setting the threshold value Rf is predetermined, all results calculated by means of the function are also predetermined since each starting value or combination of starting values is matched by an unequivocally corresponding threshold value Rf. In addition to the measured carbon dioxide concentration and/or alcohol concentration, the function can be adapted to account for other factors contributing to the reliability of measuring. Naturally, it is possible to employ a single variable threshold value or several variable threshold values or variable and fixed threshold values together. Also the subsequently described operating principles apply to variable threshold values.

FIG. 3B depicts a condition in which even the highest carbon dioxide concentration Rb measured in a long and deep-lung exhalation is lower than in the above-described normal condition. Such a decreased carbon dioxide concentration develops e.g. in a hyperventilation condition, which a subject may intentionally create by taking several deep breaths. Thus, the alcohol concentration Ra measured during this deep lung exhalation will also be lower than what it is in a normal condition without preceding deep breaths, although the blood alcohol level is the same in both instances. Hence, if the blood alcohol content were reported on the basis of an alcohol measuring result over this plateau stage F3, the result would be a value which is lower than the true existing value which was correctly represented by the alcohol concentration value of FIG. 3A. In this case, the highest measured carbon dioxide concentration Rb sets below the second threshold value R2, which situation can be reported to the operator for example as a detected carbon dioxide concentration (e.g. 3.7% $CO_2$) by a suitable alarm, by suitable further instructions to the measuring device operator or by failing to disclose the measured alcohol content or by some other means to be described hereinbelow.

Figure 3C:
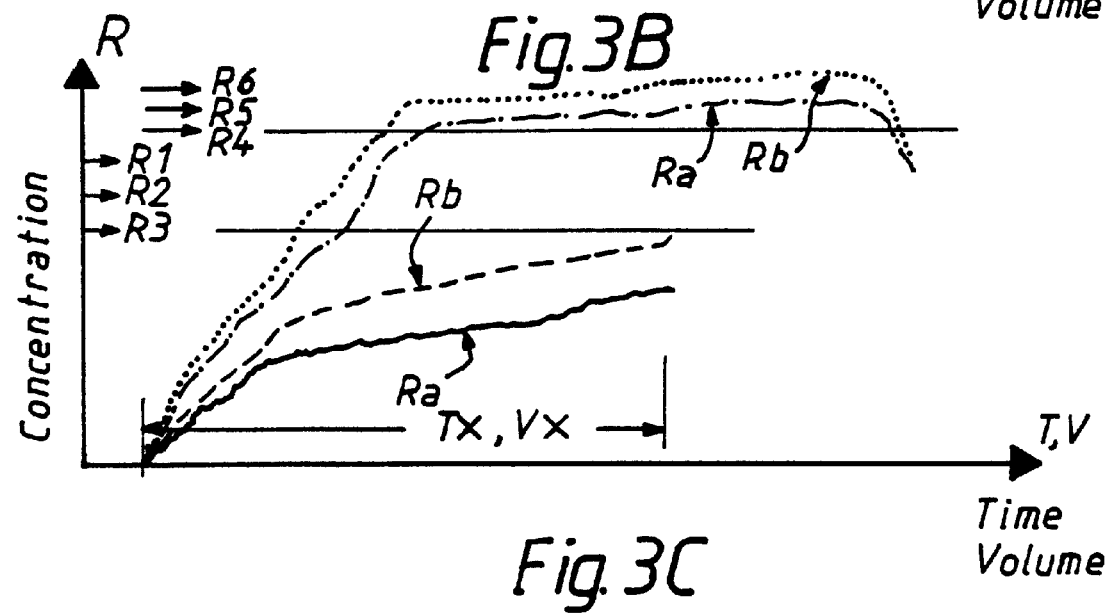
FIG. 3C illustrates by a solid line and a dashed line alcohol and carbon dioxide concentration values detected in the exhalation air stream in the case that a subject during measuring restricts or limits the exhalation volume and/or time, the blood alcohol level being the same as in the case of FIG. 3A. The figure also shows by a dash and dot line and a dotted line the case, wherein a subject prior to measuring restricts the exhaled volume and/or time and, during the course of measuring, exhales normally from the deep lungs, the blood alcohol level being the same as in the case of FIG. 3A.

FIG. 3C depicts first of all with a solid line and a dashed line a condition in which neither the carbon dioxide concentration Rb nor alcohol concentration Ra of exhalation includes any actual plateau stage F3, which indicates that a subject has not exhaled from the deep lungs but has restricted his or her exhalation during measuring. Thus, the highest detected value of carbon dioxide concentration Rb is also lower than a normal value, being in this case lower than said third lower threshold value R3. Also in this case, the conclusions drawn on the basis of alcohol concentration Ra measured from exhalation air and regarding the blood alcohol content would be too low in reference to the true blood alcohol level, since the alcohol concentration curve Ra of FIG. 3C extends at a lower level than the alcohol concentration curve produced by normal effective exhalation in a similar situation, as shown in FIG. 3A. In addition to this, it can be detected that the exhalation time Tx or exhalation volume Vx produced by restricted or reduced exhalation are lower than the maximum values Tm and Vm established in normal exhalation, as depicted in FIGS. 3A and 3B. In this case as well, the situation can be reported to the operator for example as a detected carbon dioxide concentration (e.g. 3.1% $CO_2$) by a suitable alarm, by suitable further instructions to the measuring device operator or by failing to disclose the measured alcohol concentration or by some other means to be described hereinbelow.

Secondly, FIG. 3C depicts a condition in which the carbon dioxide concentration Rb measured at the time of exhalation from the deep lungs is higher than in the above-described normal condition. Such an increased carbon dioxide concentration develops e.g. in a hypoventilation situation, wherein a subject, perhaps due to a tense condition caused by the measuring situation, may have even for a rather long time quite a shallow breathing with a small amount of air. Then, as he or she is ordered in the measuring situation to exhale from the deep lungs, the alcohol concentration Ra measured during the emerging exhalation will be higher than what it would in a normal situation without preceding shallow breaths, even though the blood alcohol content is the same in both situations. In this situation, it is possible to detect at least some sort of plateau stage and, thus, on the basis of an alcohol measuring result, the outcome would be a value which is higher than the truly valid value, which was correctly represented by the alcohol concentration value of FIG. 3A. In this case, however, the highest measured carbon dioxide concentration Rb is above the first upper threshold value R4, which situation can be reported to the operator for example as a detected carbon dioxide concentration (e.g. 6.2% $CO_2$) by means of a suitable alarm, suitable further instructions to the measuring device operator or by not disclosing the measured alcohol content or by some other means to be explained hereinbelow. In this described hypoventilation situation, the exhalation time Tx and exhalation volume Vx are usually normal, as in FIGS. 3A and 3B.

Thus, according to the above-described inventive principle, if the carbon dioxide concentration Rb measured from exhalation exceeds the above lower threshold value and/or is lower than the above-described upper threshold value, the alcohol concentration value Rae measured from the same exhalation over its plateau stage F3 or corresponding to the end of exhalation (end-tidal) will be accepted as being representative of blood alcohol content and, thus, will be reported normally to the operator. In a situation like this, the alcohol concentration measured from exhalation and the true blood alcohol level have a known reliable correlation.

On the other hand, if the carbon dioxide concentration value Rb measured from exhalation and especially if the highest carbon dioxide concentration Rb measured from exhalation, the latter being most often a value Rbe appearing at the end of exhalation (end-tidal), is lower than this lower threshold value R1 and/or R2 and/or R3 and/or respectively higher than said upper threshold value R4 and/or R5 and/or R6, at least this failure to reach and/or, respectively, the exceeding of the threshold value is output or reported to the operator or the result received on the basis of the alcohol concentration measurement is not disclosed at all or the operator is given a visual or audible alarm or the operator is supplied with instructions to carry out a new measurement after a given period of time or this obtained information is otherwise exploited.

Generally speaking, all such measurements can be categorized as being below the carbon dioxide concentration lower threshold value of the invention wherein the highest detected carbon dioxide concentration Rb fails to reach any of the lower threshold values R1–R3, no matter which stage of exhalation the measured $CO_2$-result is received from since, according to the present knowledge, the carbon dioxide concentration of exhalation, unlike the alcohol concentration, does not include concentration peaks.

As described above, the arrangement of the invention may employ either a single carbon dioxide concentration lower threshold value R1 or several lower threshold values R1-R2 or R1–R3 and/or either a single carbon dioxide concentration upper threshold value R4 or several upper threshold values R4-R5 or R4–R6, as described above.

Special measures can be undertaken according to whichever threshold value has not been reached at any given time. Thus, for example, a failure to reach the threshold value R1 depicted in the figures could be reported by way of an alarm or otherwise to the operator but the detected alcohol concentration would be disclosed nonetheless. If the detected carbon dioxide concentration fails to reach the lower threshold value R2 or exceeds the upper threshold value R5, the apparatus provides e.g. a certain fixed period after which a renewed measurement can be effected. During the time lapse it is monitored that the subject in question breathes normally. If the detected carbon dioxide value fails to reach the lower threshold value R3, the measured alcohol content shall not be reported to the operator and, instead, the apparatus delivers an instruction to subject the person undergoing testing to a blood test. Thus, the further actions can be ordered according to how low or respectively how high a level the detected carbon dioxide concentration of exhalation falls to or respectively rises to, whereby at least a major failure would lead to more radical actions.

However, there is nothing to exclude notifying the operator of the carbon dioxide concentration Rb even in the case that the latter is higher than said highest determined lower threshold value R1 or lower than the lowest determined upper threshold value R4, in other words, the carbon dioxide concentration can always be reported to the operator, if desired.

In addition to the utilization of the above-described carbon dioxide measuring and the threshold values defined therefor, the reliability of alcohol measuring can be improved by one or more of the following procedures. The plateau sections F3 occurring in the exhalation carbon dioxide concentration and alcohol concentration can be detected by measuring either carbon dioxide concentration Rb or alcohol concentration Ra over an exhalation time Tm, either continuously or several times. Thus, the plateau section F3 is verifiable by comparing two or more successive measured values and differences $\Delta Ra$ and/or $\Delta Rb$ therebetween. In case $\Delta Ra$ and/or $\Delta Rb$ over a given time difference $\Delta T$ or volume difference $\Delta V$ is smaller than a predetermined value, it can be concluded that exhalation has reached the plateau section F3 and in this respect a reliable alcohol measurement could be effected. As another alternative, it is possible to measure an exhalation time Tx or an exhalation volume Vx and to compare these with sufficiently high but realistic maximum values Tm and Vm provided by normal exhalation and, if the former are to a sufficient degree lower than these maximum values Tm and Vm, it can be concluded that a subject has not taken a sufficiently clear breath from the deep lungs. The output of alcohol content is produced by using either the average or weighted average of alcohol concentration Ra calculated over the duration or some portion of the duration of the plateau section F3 or a value picked up at some point in the plateau section or the highest detected alcohol concentration value, which in most cases is the value Rae near the end of exhalation.

The above-described detection of the plateau section F3 by means of the discrimination quantities $\Delta Ra$ and/or $\Delta Rb$ and/or by means of the exhalation time Tx or exhalation volume Vx is in the method of the invention intended for yielding secondary, i.e. just additional information and reliability. What is essential in view of producing a correct alcohol measuring result is that the carbon dioxide concentration of exhalation be sufficiently high yet not excessively high, whereby it is possible to draw correct conclusions very reliably regarding blood alcohol content on the basis of alcohol concentration Ra measured from exhalation over the same stage. The detection of the plateau stage F3 by any of the above procedures further adds to the reliability at which the measured alcohol concentration Ra is used for drawing conclusions regarding the blood alcohol content.

Figure 1:
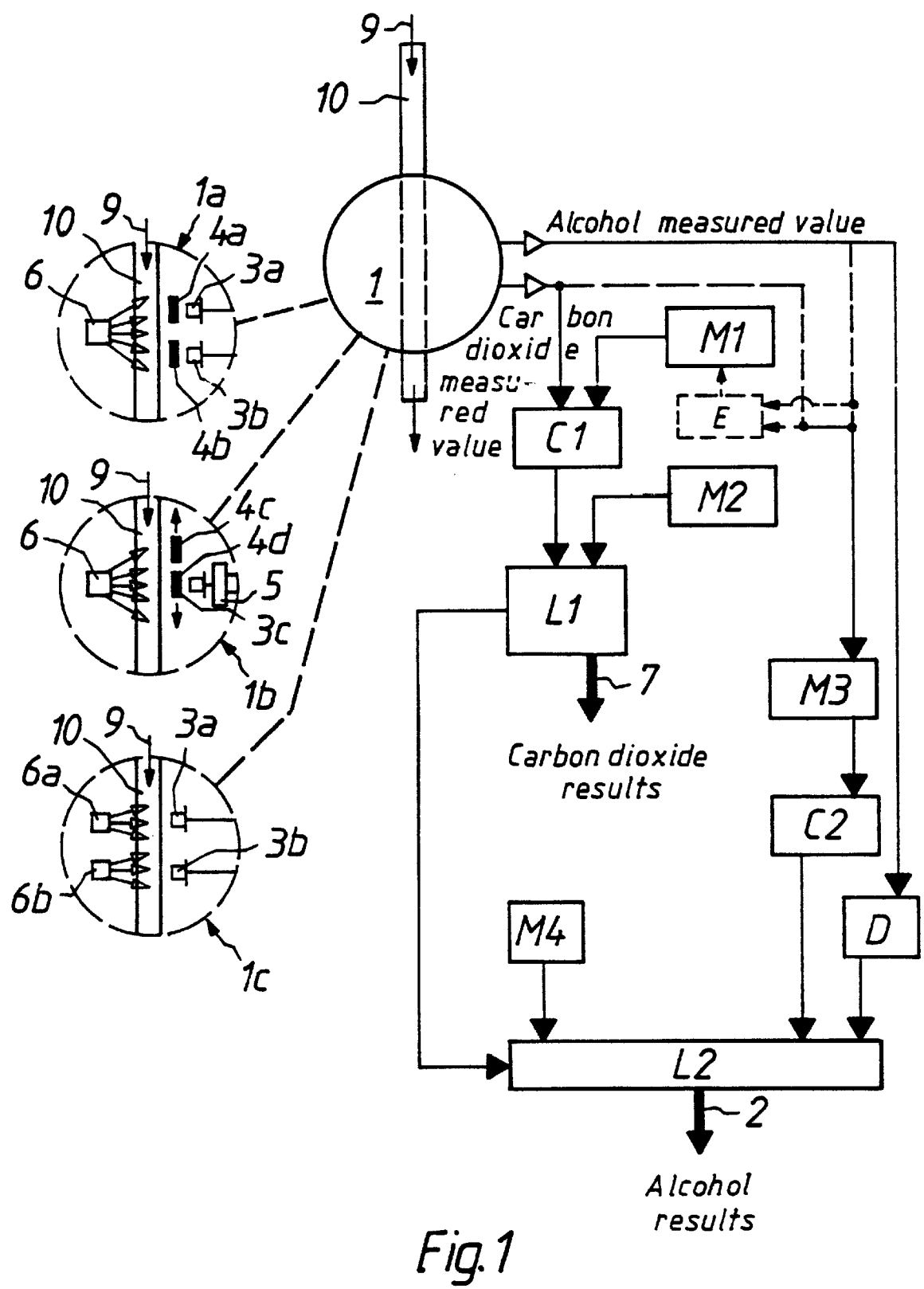
FIG. 1 shows one embodiment for an apparatus of the invention in a schematic view.
Figure 2:
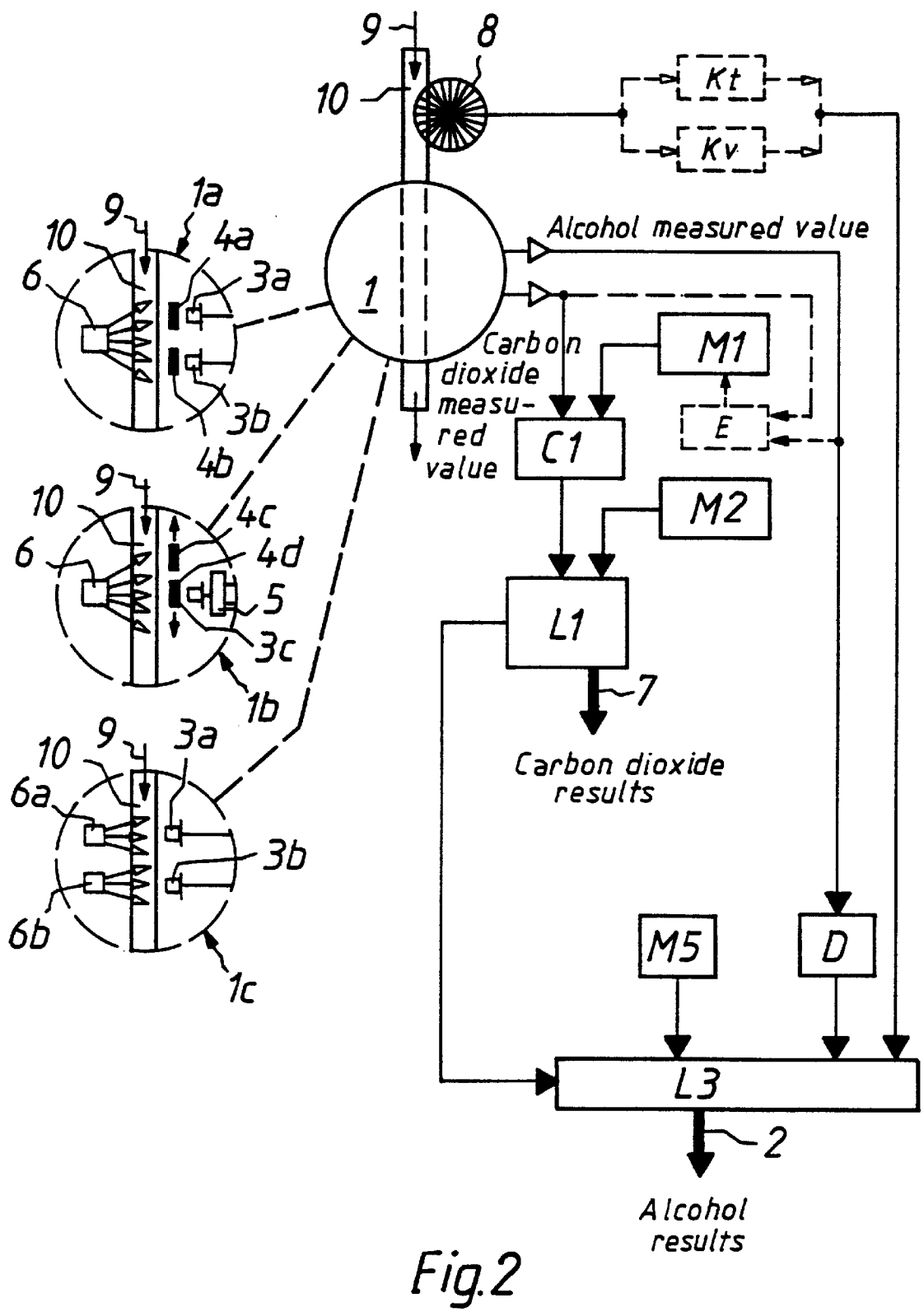
FIG. 2 shows a second embodiment for an apparatus of the invention in a schematic view.

FIGS. 1 and 2 illustrate equipment for carrying out the above-described method. First of all, the apparatus includes a conventional flow channel 10 through which a subject being examined blows an exhalation air stream 9 and the flow channel is provided with sensor elements 1 for measuring alcohol concentration Ra as well as carbon dioxide concentration Rb. Furthermore, the apparatus includes necessary first output elements 2 for delivering at least a measured alcohol concentration result to the operator, if necessary. For a display of carbon dioxide concentration according to the invention, an alarm or some other application, the apparatus of the invention also includes second output elements 7.

The sensor elements 1 comprise an infrared radiation source 6 for radiating through the channel 10 and, thus, through the exhalation air stream 9. In addition, the sensor elements include either two optical infrared sensors 3a and 3b, each of which is preceded by a band-pass filter 4a and 4b transmissive to the wavelength to be measured thereby, or alternatively a single optical infrared sensor 3c and two replaceable band-pass filters 4c and 4d located in front of the latter and transmissive to each wavelength to be measured. Hence, in the former case 1a, one filter-sensor unit 4a, 3a measures alcohol concentration and the other filter-sensor unit 4b, 3b measures carbon dioxide concentration in the respiratory air stream 9. Thus, the measuring can be completely or nearly continuous. In the latter case 1b, in front of the infrared sensor 3c is alternately replaced the filter 4c for alcohol concentration and the filter 4d for carbon dioxide concentration in view of alternately measuring the alcohol concentration and carbon dioxide concentration of the respiratory air stream. This latter case further requires a control element 5 for carrying out concentration measurements at fixed intervals and to guide the measured alcohol concentration values and measured carbon dioxide concentration values to a correct location in the apparatus for further processing. A third alternative is to employ two sensors 3a and 3b and, in addition to this, two infrared radiation sources 6a and 6b, one being trained at the first sensor and the other at the second sensor. This enables a total or nearly continuous measurement of both alcohol and carbon dioxide. In this configuration, it is not absolutely necessary to have band-pass filters in front of the sensors provided that the infrared radiation sources are emitting over sufficiently narrow bands.

According to the invention, the apparatus includes a first memory M1, in which the fixed lower threshold value R1, two fixed lower threshold values R1 and R2 or three fixed lower threshold values R1–R3 or the variable lower threshold value Rf or variable lower threshold values and/or, respectively, the upper threshold value R4, two fixed upper threshold values R4 and R5 or three fixed upper threshold values R4–R6 or the variable upper threshold value Rg or variable upper threshold values, described above in reference to the method, are previously stored before setting the apparatus in operation. In order to compare these threshold values stored in memory M1 and the carbon dioxide concentration measured from exhalation air stream 9, the apparatus includes a comparing element C1 whose output provides information about which one or which ones of these threshold values the carbon dioxide concentration Rb measured at any given time fails to reach or exceeds. This information is forwarded to a first logic element L1. To this first logic element L1 is also connected a second memory M2 in which are stored outputs of a previously set type. These previously set type of outputs are, as already described above in reference to the method: a) a visual or audible alarm; b) which one of the lower threshold values R1 or R2 or R3 or Rf is not reached or the upper threshold values R4 or R5 or R6 or Rg is exceeded, i.e. identification of seriousness of the failure or respectively that of the exceeding; c) the output of measured carbon dioxide concentration and/or a measured carbon dioxide concentration curve; d) omission to disclose the result obtained on the basis of measured alcohol concentration; e) the apparatus issues, according to the degree of seriousness of the failure or exceeding or at any time a failure or exceeding occurs, an instruction for carrying out a measurement after a given period of time, whereby this given period of time can be adapted to depend on how grave is the failure to reach or the exceeding of a threshold value in reference to the threshold value itself or to the highest lower threshold value R1 or in reference to the lowest upper threshold value R4. Just these several threshold values described above can be used as an indicator for the seriousness of failure/exceeding, such that the failure to reach the higher threshold value R1 and exceeding the lowest upper threshold value R4 is less serious and the failure to reach the lowest lower threshold value R3 is the most serious and the failure to reach the middle lower threshold value R2 lies therebetween and, respectively, exceeding the highest upper threshold value R6 is the gravest and exceeding the middle upper threshold value R5 lies therebetween. It is also possible to use just one lower threshold value and upper threshold value and to estimate the failure to reach the threshold value from there downwards and, respectively, the exceeding of the threshold value from there upwards linearly or otherwise according to the degree of change. The procedure is similar to the above when using variable threshold values Rf. On the basis of this above-described information stored in the second memory M2, the first logic elements hence produce one or more of these previously set type of outputs regarding carbon dioxide by means of the second output elements 7 always according to whether the carbon dioxide concentration measured at a given time fails to reach or exceeds the predetermined threshold values. In addition to this, the first logic element L1 delivers this information to a second or third logic element L2 or L3 to be described hereinbelow.

The measured alcohol value coming from the sensor elements 1 progresses first to a calculator D which, according to a predesigned programming, if there are several measured alcohol values, effects the calculation of an average or, in a predetermined manner, a weighted average of these or the selection of the highest of measured alcohol values received. This calculated information or several pieces of calculated information advance further to the second or third logic element L2 or L3.

The embodiment of FIG. 1 is further provided with a third memory M3 which is supplied with alcohol concentration measuring values and/or carbon dioxide concentration measuring values measured during the same exhalation for being stored therein. This third memory M3 is further connected to a second comparing element C2, wherein the latest one of the above stored alcohol concentration measuring values and/or carbon dioxide concentration measuring values is compared to the preceding one or ones and the obtained difference value ΔRa and/or respectively ΔRb is forwarded to the second logic element L2. The second logic element L2 compares the difference value ΔRa and/or respectively ΔRb to the maximum values stored in a fourth memory M4 and, if this difference value or difference values are lower than the stored maximum values, the apparatus concludes that the measured results have been obtained from the plateau stage F3 of exhalation 9 and, thus, in this respect, the alcohol measuring output is possible by means of the elements 2 on the basis of a value received from the calculator D. However, this possible output is restricted by means of a restricting connection leading from the first logic element L1 to the second logic element L2 for preventing, if necessary, the second logic element L2 from producing an output of the measured alcohol in case the carbon dioxide concentration detected by the first logic element L1 is too low or too high.

In the embodiment of FIG. 2, the channel 10 for exhalation air stream 9 is provided with an instrument 8, which can be e.g. a rotating blade wheel, a turbine or some other pressure-difference recognizing element for detecting the passage of exhalation air stream 9 through the channel 10. In one alternative, the apparatus further includes an element Kv measuring the volume Vx of this exhalation air stream 9, whereby the instrument 8 must of course be of the type that delivers to the measuring element Kv a quantity which is proportional to the volume flow. In second alternative, the apparatus further includes, and instead of the element Kv, an element Kt measuring the time Tx of exhalation air stream 9, whereby the instrument 8 must only recognize the existence of the air stream 9. These required minimum values for exhalation volume Vx and exhalation time Tx are stored in a fifth memory M5. The third logic element L3 compares values received from the volume measuring element Kv and/or duration measuring element Kt with the values stored in the memory M5 and, in case the achieved values are higher than these preset values, the apparatus concludes that the measured results have been received from the plateau stage F3 and, thus, in this respect, the alcohol measuring output is possible by means of the elements 2 on the basis of a value received from the calculator D. However, this possible output is restricted by means of a restricting connection leading from the first logic element L1 to the second logic element L2 for preventing, if necessary, the second logic element L2 from producing an output of the measured alcohol in case the carbon dioxide concentration detected by the first logic element L1 is too low or too high.

In case the apparatus of the invention is adapted to measure just one alcohol concentration value and just one carbon dioxide concentration value, said apparatus requires neither the third memory M3, fourth memory M4 nor the second comparing element C2. Thus, the calculator D is possibly also unnecessary as a single measured value cannot be subjected calculations. If the apparatus of the invention is adapted to operate without measuring the exhalation volume Vx and time Tx, said apparatus requires neither the instrument 8, measuring elements Kv or Kt nor the fifth memory M5. Even if stripped of these mentioned components, the apparatus of the invention operates as intended but, generally, it is preferred that some of these functions be included in the apparatus for enhanced reliability. It is obvious that, in practice, the apparatus can be designed by using a wide range of different components.

The dotted lines in FIGS. 1 and 2 indicate a threshold value calculator E for calculating, according to a function stored therein, the variable threshold value Rf or variable threshold values on the basis of the measured alcohol concentration value Ra and/or measured carbon dioxide concentration value Rb. This threshold value information is transferred in this case just for the duration of a particular measurement into the first memory M1 for operation. The first memory M1 is wiped clean of the threshold value Rf and respectively Rg prior to storing a new threshold value to be calculated in connection with the next measurement. Of course, this threshold value calculator E is included in the apparatus only in the case that the measuring arrangement includes the use of a predetermined variable threshold value.

I claim:

1. A method for obtaining a reliable blood alcohol concentration value from respiratory gases of a subject undergoing examination, the subject respiring gases in a respiratory cycle having an exhalation phase with exhalation stages, a respiratory cycle exhalation phase suitable for providing a reliable blood alcohol concentration value having a plateau stage, the plateau stage having a beginning and a concluding portion, respiratory gases of the subject exhaled in the plateau stage comprising alveolar gas of the subject, said method comprising the steps of:

sampling the respiratory gases of the subject during the exhalation phase to obtain a plurality of $CO_2$ concentration measurements, the sampling occurring at successive points in time in an exhalation phase and including points occurring in the plateau stage of a suitable exhalation phase;

sampling the respiratory gases of the subject during the exhalation phase at at least one point in time having a predetermined temporal relationship to the concluding portion of the plateau stage to obtain at least one alcohol concentration measurement;

comparing a $CO_2$ concentration measurement obtained from the respiratory gases to a predetermined $CO_2$ concentration threshold value to determine whether the $CO_2$ concentration measurement is greater or less than the predetermined $CO_2$ concentration value;

detecting from the measurements of $CO_2$ concentration obtained from the sampling at successive points in time, the existence of a plateau stage in the exhalation phase being sampled;

if the existence of a plateau stage is detected and if the $CO_2$ concentration measurement exceeds the predetermined threshold value, producing, as reliable, a blood alcohol concentration value output using the at least one alcohol concentration value measurement; and if at least one of the conditions comprising the existence of a plateau stage and the $CO_2$ concentration measurement exceeding the predetermined threshold value is not present, providing an output differing from that produced when the conditions are present.

2. A method as set forth in claim 1, wherein the step of sampling respiratory gases to obtain at least one alcohol concentration measurement is further defined as obtaining a plurality of alcohol concentration measurement.

3. A method for obtaining a reliable blood alcohol concentration value from respiratory gases of a subject undergoing examination, the subject respiring gases in a respiratory cycle having an exhalation phase with exhalation stages, a respiratory cycle exhalation phase suitable for providing a reliable blood alcohol concentration value having a plateau stage, the plateau stage having a beginning and a concluding portion, respiratory gases of the subject exhaled in the plateau stage comprising alveolar gas of the subject, said method comprising the steps of:

sampling the respiratory gases of the subject during the exhalation phase to obtain a plurality of alcohol concentration measurements, the sampling occurring at successive points in time in the plateau stage of a suitable exhalation phase and including a point having a predetermined temporal relationship to the concluding portion of the plateau stage;

sampling the respiratory gases of the subject during the exhalation phase at at least one point in time to obtain a $CO_2$ concentration measurement;

comparing the $CO_2$ concentration measurement obtained from the respiratory gases to a predetermined $CO_2$ concentration threshold value to determine whether the $CO_2$ concentration measurement is greater or less than the predetermined $CO_2$ concentration value;

detecting from the measurements of alcohol concentration obtained from the sampling at successive points in time, the existence of a plateau stage in the exhalation phase being sampled;

if the existence of a plateau stage is detected and if the $CO_2$ concentration measurement exceeds the predetermined threshold value, producing, as reliable, a blood alcohol concentration value output using the alcohol concentration value measurement obtained at the point having the predetermined temporal relationship to the concluding portion of the plateau stage; and if at least one of the conditions comprising the existence of a plateau stage and the $Co_2$ concentration measurement exceeding the predetermined threshold value is not present, providing an output differing from that produced when the conditions are present.

4. A method as set forth in claim 3 wherein the step of sampling respiratory gases to obtain at least one $CO_2$ concentration measurement is further defined as obtaining a plurality of $CO_2$ concentration measurement.

5. A method for obtaining a reliable blood alcohol concentration value from respiratory gases of a subject undergoing examination, the subject respiring gases in a respiratory cycle having an exhalation phase with exhalation stages, a respiratory cycle exhalation phase suitable for providing a reliable blood alcohol concentration value having a plateau stage, the plateau stage having a beginning and a concluding portion, respiratory gases of the subject exhaled in the plateau stage comprising alveolar gas of the subject, said method comprising the steps of:

sampling the respiratory gases of the subject during the exhalation phase to obtain at least one $CO_2$ concentration measurement;

sampling the respiratory gases of the subject during the exhalation phase at at least one point in time having a predetermined temporal relationship to the concluding portion of the plateau stage to obtain an alcohol concentration measurement;

comparing the $CO_2$ concentration measurement obtained from the respiratory gases to a predetermined $CO_2$ concentration threshold value to determine whether $CO_2$ concentration measurement is greater or less than the predetermined $CO_2$ concentration value;

detecting from the measurement of exhaled volume or exhalation phase duration, the existence of a plateau stage in the exhalation phase being sampled;

if the existence of a plateau stage is detected and if the $CO_2$ concentration measurement exceeds the predetermined threshold value, producing, as reliable, a blood alcohol concentration value output using the alcohol concentration value measurement; and if at least one of the conditions comprising the existence of a plateau stage and the $CO_2$ concentration measurement exceeding the predetermined threshold value is not present, providing an output differing from that produced when the conditions are present.

6. A method as set forth in claim 1, 3, 2, or 4 wherein the step of detecting the plateau stage is further defined comparing measurements obtained at successive points in time in the sampling step and detecting the plateau stage from the magnitude of the difference in the successive measurements.

7. A method as set forth in claim 1, 3, or 5 wherein the comparing step is further defined as determining whether a plateau stage $CO_2$ concentration measurement is greater or less than a predetermined lower $CO_2$ concentration threshold value.

8. A method as set forth in claim 1, 3 or 5 further including the step of providing a predetermined, selected output if a $CO_2$ concentration measurement fails to exceed the lower threshold value.

9. A method as set forth in claim 8 wherein the predetermined selected output is at least one of; producing an alarm, disclosing a blood alcohol concentration value, not disclosing blood alcohol concentration values, disclosing $CO_2$ concentration measurement properties, repeating the steps of the method, and issuing instructions to an operator.

10. A method as set forth in claim 7 further including the step of establishing a lower $CO_2$ concentration threshold value in a range of 3–5% $CO_2$ in the respiratory gases.

11. A method as set forth in claim 10 further defined as establishing a lower $CO_2$ concentration threshold value equal to or less than 4.7% $CO_2$ in the respiratory gases.

12. A method as set forth in claim 7 further including the step of establishing a variable lower $CO_2$ concentration threshold value.

13. A method as set forth in claim 7 further including the step of establishing a plurality of lower $CO_2$ concentration threshold values, each corresponding to a different concentration of $CO_2$ in the respiratory gases, and wherein the producing step is carried out if a $CO_2$ concentration measurement exceeds the highest lower threshold value.

14. A method as set forth in claim 13 further defined as establishing a first lower $CO_2$ concentration threshold value in a range of 4.0–4.7% $CO_2$ in the respiratory gases, establishing a second lower $CO_2$ concentration threshold value in a range of 3.5–4% $CO_2$ in the respiratory gases; and establishing a third lower $CO_2$ concentration threshold value in a range of 3.0–3.5% $CO_2$ in the respiratory gases.

15. A method as set forth in claim 13 further including the step of providing a predetermined selected output if a $CO_2$ concentration measurement fails to exceed one of the lower $CO_2$ concentration threshold values, the output being selected in accordance with a determination of which threshold value the $CO_2$ concentration measurement fails to exceed.

16. A method as set forth in claim 7 wherein the comparing step is further defined as comparing the $CO_2$ concentration measurement to an upper $CO_2$ concentration threshold value and as determining whether a $CO_2$ concentration measurement obtained from the respiratory gases in the plateau stage is greater or less than an upper $CO_2$ concentration threshold value and wherein the producing step is further defined as producing, when the $CO_2$ concentration measurement exceeds the lower threshold value and is less than the upper threshold value, a blood alcohol concentration value output using the at least one alcohol concentration measurement.

17. A method as set forth in claim 16 further including the step of establishing an upper $CO_2$ concentration threshold value in a range of 5.3–7% $CO_2$ in the respiratory gases.

18. A method as set forth in claim 10 further including the step of establishing an upper $CO_2$ concentration threshold value in a range of 5.3–7% $CO_2$ in the respiratory gases, wherein the comparing step is further defined as determining whether a $CO_2$ concentration measurement is greater or less than an upper $CO_2$ concentration threshold value, and wherein the producing step is further defined as producing, when a $CO_2$ concentration measurement exceeds the lower threshold value and is less than the upper threshold value, a blood alcohol concentration value output using the at least one alcohol concentration measurement.

19. A method as set forth in claim 17 further defined as establishing an upper $CO_2$ concentration threshold value equal to or greater than 5.5% $CO_2$ in the respiratory gases.

20. A method as set forth in claim 16 further including the step of establishing a variable upper $CO_2$ concentration threshold value.

21. A method as set forth in claim 16 further including the step of establishing a plurality of upper $CO_2$ concentration threshold values, each corresponding to a different concentration of $CO_2$ in the respiratory gases.

22. A method as set forth in claim 21 further defined as establishing a first upper $CO_2$ concentration threshold value of 5.5–6.0% $CO_2$ in the respiratory gases, establishing a second upper $CO_2$ concentration threshold value of 6.0–6.5% $CO_2$ in the respiratory gases; and establishing a third upper $CO_2$ concentration threshold value of 6.5–7.0% $CO_2$ in the respiratory gases.

23. A method as set forth in claim 21 further including the step of providing a predetermined selected output if a $CO_2$ concentration measurement exceeds one of the upper $CO_2$ concentration threshold values, the output being selected in accordance with a determination of which of the threshold values the $CO_2$ concentration measurement exceeds.

24. A method for obtaining a reliable blood alcohol concentration value from respiratory gases of a subject undergoing examination, the subject respiring gases in a respiratory cycle having an exhalation phase with exhalation stages, a respiratory cycle exhalation phase suitable for providing a reliable blood alcohol concentration value having a plateau stage, the plateau stage having a beginning and a concluding portion, respiratory gases of the subject exhaled in the plateau stage comprising alveolar gas of the subject, said method comprising the steps of:

sampling the respiratory gases of the subject during the exhalation phase to obtain a plurality of $CO_2$ concentration measurements, the sampling occurring at successive points in time in an exhalation phase and including points occurring in the plateau stage of a suitable exhalation phase;

sampling the respiratory gases of the subject during the exhalation phase at at least one point in time having a predetermined temporal relationship to the concluding portion of the plateau stage to obtain at least one alcohol concentration measurement;

comparing a $CO_2$ concentration measurement obtained from the respiratory gases to a predetermined $CO_2$ concentration threshold value to determine whether the $CO_2$ concentration measurement is greater or less than the predetermined $CO_2$ concentration value;

detecting from the measurements of $CO_2$ concentration obtained from the sampling at successive points in time, the existence of a plateau stage in the exhalation phase being sampled;

if the existence of a plateau stage is detected and if the $CO_2$ concentration measurement is less than the predetermined threshold value, producing, as reliable, a blood alcohol concentration value output using the at least one alcohol concentration value measurement; and if at least one of the conditions comprising the existence of a plateau stage and the $CO_2$ concentration measurement being less than the predetermined threshold value is not present, providing an output differing from that produced when the conditions are present.

25. A method as set forth in claim 24, wherein the step of sampling respiratory gases to obtain at least one alcohol concentration measurement is further defined as obtaining a plurality of alcohol concentration measurements.

26. A method for obtaining a reliable blood alcohol concentration value from respiratory gases of a subject undergoing examination, the subject respiring gases in a respiratory cycle having an exhalation phase with exhalation stages, a respiratory cycle exhalation phase suitable for providing a reliable blood alcohol concentration value having a plateau stage, the plateau stage having a beginning and a concluding portion, respiratory gases of the subject exhaled in the plateau stage comprising alveolar gas of the subject, said method comprising the steps of:
  sampling the respiratory gases of the subject during the exhalation phase to obtain a plurality of alcohol concentration measurements, the sampling occurring at successive points in time in the plateau stage of a suitable exhalation phase and including a point having a predetermined temporal relationship to the concluding portion of the plateau stage;
  sampling the respiratory gases of the subject during the exhalation phase at at least one point in time to obtain a $CO_2$ concentration measurement;
  comparing the $CO_2$ concentration measurement obtained from the respiratory gases to a predetermined $CO_2$ concentration threshold value to determine whether $CO_2$ concentration measurement is greater or less than the predetermined $CO_2$ concentration value;
  detecting from the measurements of alcohol concentration obtained from the sampling at successive points in time, the existence of a plateau stage in the exhalation phase being sampled;
  if the existence of a plateau stage is detected and if the $CO_2$ concentration measurement is less than the predetermined threshold value, producing, as reliable, a blood alcohol concentration value output using the alcohol concentration value measurement obtained at the point having the predetermined temporal relationship to the concluding portion of the plateau stage; and
  if at least one of the conditions comprising the existence of a plateau stage and the $CO_2$ concentration measurement being less than the predetermined threshold value is not present, providing an output differing from that produced when the conditions are present.

27. A method as set forth in claim 26 wherein the step of sampling respiratory gases to obtain at least one $CO_2$ concentration measurement is further defined as obtaining a plurality of $CO_2$ concentration measurements.

28. A method for obtaining a reliable blood alcohol concentration value from respiratory gases of a subject undergoing examination, the subject respiring gases in a respiratory cycle having an exhalation phase with exhalation stages, a respiratory cycle exhalation phase suitable for providing a reliable blood alcohol concentration value having a plateau stage, the plateau stage having a beginning and a concluding portion, respiratory gases of the subject exhaled in the plateau stage comprising alveolar gas of the subject, said method comprising the steps of:
  sampling the respiratory gases of the subject during the exhalation phase to obtain at least one $CO_2$ concentration measurement;
  sampling the respiratory gases of the subject during the exhalation phase at at least one point in time having a predetermined temporal relationship to the concluding portion of the plateau stage to obtain an alcohol concentration measurement;
  comparing the $CO_2$ concentration measurement obtained from the respiratory gases to a predetermined $CO_2$ concentration threshold value to determine whether $CO_2$ concentration measurement is greater or less than the predetermined $CO_2$ concentration value;
  detecting from the measurement of exhaled volume or exhalation phase duration, the existence of a plateau stage in the exhalation phase being sampled;
  if the existence of a plateau stage is detected and if the $CO_2$ concentration measurement is less than the predetermined threshold value, producing, as reliable, a blood alcohol concentration value output using the alcohol concentration value measurement; and
  if at least one of the conditions comprising the existence of a plateau stage and the $CO_2$ concentration measurements being less than the predetermined threshold value is not present, providing an output differing from that produced when the conditions are present.

29. A method as set forth in claim 26, 25, or 27 wherein the step of detecting the plateau stage is further defined comparing measurements obtained at successive points in time in the sampling step and detecting the plateau stage from the magnitude of the difference in the successive measurements.

30. A method as set forth in claim 24, 26, or 28, wherein the determining step is further defined as determining whether a plateau stage $CO_2$ concentration measurement is greater or less than a predetermined upper $CO_2$ concentration threshold value.

31. A method as set forth in claim 30 further including the step of establishing an upper $CO_2$ concentration threshold value in a range of 5.3–7% $CO_2$ in the respiratory gases.

32. A method as set forth in claim 31 further defined as establishing an upper $CO_2$ concentration threshold value equal to or greater than 5.5% $CO_2$ in the respiratory gases.

33. A method as set forth in claim 30 further including the step of establishing a variable upper $CO_2$ concentration threshold value.

34. A method as set forth in claim 30 further including the step of establishing a plurality of upper $CO_2$ concentration threshold values, each corresponding to a different concentration of $CO_2$ in the respiratory gases, and wherein the producing step is carried out if a $CO_2$ concentration measurement is less than the lowest upper threshold value.

35. A method as set forth in claim 34 further defined as establishing a first upper $CO_2$ concentration threshold value in a range of 5.5–6.0% $CO_2$ in the respiratory gases, establishing a second upper $CO_2$ concentration threshold value in a range of 6.0–6.5% $CO_2$ in the respiratory gases; and establishing a third upper $CO_2$ concentration threshold value in a range of 6.5–7.0% $CO_2$ in the respiratory gases.

36. A method as set forth in claim 34 further including the step of providing a predetermined selected output if the $CO_2$ concentration measurement exceeds one of the upper $CO_2$ concentration threshold values, the output being selected in accordance with a determination of which of the threshold values the $CO_2$ concentration measurement exceeds.

37. A method as set forth in claim 24, 26, or 28 further including the step of providing a predetermined, selected output if the $CO_2$ concentration measurement exceeds the upper threshold value.

38. A method as set forth in claim 37 wherein the predetermined selected output is at least one of; producing an alarm, disclosing a blood alcohol concentration value, not disclosing blood alcohol concentration values, disclosing $CO_2$ concentration measurement properties, repeating the steps of the method, and issuing instructions to an operator.

39. A method as set forth in claim 1, 3, 5, 24, or 24 wherein the sampling is carried out to obtain a $CO_2$ concentration measurement and alcohol concentration measurement substantially simultaneously.

40. A method as set forth in claim 1, 3, 5, 24, 26, or 38 wherein the sampling is carried out with a time delay existing between obtaining a $CO_2$ concentration measurement and an alcohol concentration measurement.

41. A method as set forth in claim 1, 3, 5, 24, 26, or 28 wherein the producing step is further defined as producing a blood alcohol concentration value using averaging of alcohol concentration measurements.

42. A method as set forth in claim 1, 3, 5, 24, 26, or 28 wherein a plurality of alcohol concentration measurements are obtained and wherein the producing step is further defined as producing a blood alcohol concentration value output using the highest alcohol concentration measurement.

43. A method as set forth in claims 1, 3, 5, 24, 26, or 28 further including the step of producing a measured $CO_2$ concentration value.

44. A method as set forth in claims 1, 3, 5, 24, 26, or 28 wherein the sampling step is further defined as using the infrared absorption properties of the $CO_2$ and alcohol in the respiratory gases.

45. Apparatus for obtaining a reliable blood alcohol concentration value from respiratory gases of a subject undergoing examination, the subject respiring gases in a respiratory cycle having an exhalation phase with exhalation stages, a respiratory cycle exhalation phase suitable for providing a reliable blood alcohol concentration value having a plateau stage, the plateau stage having a beginning and a concluding portion, respiratory gases of the subject exhaled in the plateau stage comprising alveolar gas of the subject, said apparatus comprising:

sensor means (1) for sampling the respiratory gases of the subject during the exhalation phase, including the plateau stage of a suitable exhalation phase, to obtain $CO_2$ concentration measurement data and alcohol concentration measurement data, said data having at least one alcohol concentration measurement obtained at a point in time having a predetermined temporal relationship to the concluding portion of the plateau stage;

first memory means (M3) coupled to said sensor means for storing at least one of alcohol concentration measurement data and $CO_2$ concentration measurement data;

first comparing means (C2) coupled to said first memory means for comparing a given alcohol concentration measurement or carbon dioxide concentration measurement with an earlier measurement of the respective quantity to detect the exhalation phase plateau stage (F3) from a difference between the given and earlier concentration measurements;

second memory means (M1) for storing at least one predetermined $CO_2$ concentration threshold value;

second comparing means (C1) coupled to said sensor means and said second memory means for a comparing $CO_2$ measurement to said threshold value and producing an indicative comparison result signifying that the relationship of the $CO_2$ concentration measurement to the threshold value is such that a respiratory gas alcohol concentration measurement is capable of accurately indicating blood alcohol concentration; and output means (2) coupled to said sensor means, said first comparing means, and said second comparing means and responsive to the detection of the existence of a plateau stage and the indicative comparison result of said second comparing element for producing, as reliable, a blood alcohol concentration value output using the at least one alcohol concentration measurement, and in the absence of at least one of the plateau stage detection and indicative comparison result, providing an output differing from that produced when such conditions are present.

46. An apparatus as set forth in claim 45 wherein said first comparing element (C2) produces a difference value between the given and earlier measurements, wherein said apparatus includes third memory means (M4) storing a reference value and wherein said output means includes logic means (L2) for comparing the reference value and the difference value for detecting the plateau stage of the exhalation phase.

47. Apparatus for obtaining a reliable blood alcohol concentration value from respiratory gases of a subject undergoing examination, the subject respiring gases in a respiratory cycle having an exhalation phase with exhalation stages, a respiratory cycle exhalation phase suitable for providing a reliable blood alcohol concentration value having a plateau stage, the plateau stage having a beginning and a concluding portion, respiratory gases of the subject exhaled in the plateau stage comprising alveolar gas of the subject, said apparatus comprising:

sensor means (1) for sampling the respiratory gases of the subject in the exhalation phase, including the plateau stage of a suitable exhalation phase, to obtain at least one $CO_2$ concentration measurement and at least one alcohol concentration measurement obtained at a point in time having a predetermined temporal relationship to the concluding portion of the plateau stage;

measuring means for measuring at least one of the volume of exhaled respiratory gases or the duration of the exhalation phase;

first memory means (M5) for storing a reference value for the quantity measured by said measuring means;

first comparing means (L3) coupled to said measuring means and said first memory means for comparing the measured quantity with the reference value to detect an exhalation phase plateau stage (F3);

second memory means (M1) for storing at least one predetermined $CO_2$ concentration threshold value;

second comparing means (C1) coupled to said sensor means and said second memory means for comparing a $CO_2$ measurement to said threshold value and producing an indicative comparison result signifying that the relationship of the $CO_2$ concentration measurement to the threshold value is such that a respiratory gas alcohol concentration measurement is capable of accurately indicating blood alcohol concentration; and output means (2) coupled to said sensor means, said first comparing means, and said second comparing means and responsive to the detection of the existence of the plateau stage and the indicative comparison result of said second comparing element for producing, as reliable, a blood alcohol concentration value output using the at least one alcohol concentration measurement, and in the absence of at least one of the plateau stage detection and indicative comparison result, providing an output differing from that produced when such conditions are present.

48. An apparatus as set forth in claim 45 or 47, wherein said second memory means is further defined as storing a lower $CO_2$ concentration threshold value and wherein said comparing element provides said indicative comparison result when the $CO_2$ concentration measurement exceeds the lower $CO_2$ concentration threshold value.

49. An apparatus as set forth in claim 48 wherein said second memory means is further defined as storing an upper $CO_2$ concentration threshold value and wherein said second comparing element provides said indicative comparison result when the $CO_2$ concentration measurement is less than the upper $CO_2$ concentration threshold value.

50. An apparatus as set forth in claim 49 wherein said second memory means is further defined as storing a plurality of lower and upper $CO_2$ concentration threshold values.

51. An apparatus as set forth in claim 48 wherein said second memory means is further defined as storing a plurality of lower $CO_2$ concentration threshold values.

52. The apparatus as set forth in claim 51 wherein said logic element (L1) is further defined as providing a selected result if the $CO_2$ concentration measurement fails to exceed a given lower threshold value, the output being selected in accordance with a determination of which threshold value the $CO_2$ concentration fails to exceed.

53. An apparatus as set forth in claim 48 further including a logic element (L1) coupled to said second comparing element (C1) for producing a predetermined selected output if the $CO_2$ concentration measurement fails to exceed the lower threshold value.

54. An apparatus as set forth in claim 45 or 47 wherein said second memory means is further defined as storing an upper $CO_2$ concentration threshold value and wherein said second comparing element provides said indicative comparison result when the $CO_2$ concentration measurement is less than the upper $CO_2$ concentration threshold value.

55. An apparatus as set forth in claim 54 wherein said second memory means is further defined as storing a plurality of upper $CO_2$ concentration threshold values.

56. The apparatus as set forth in claim 55 wherein said logic element (L1) is further defined as providing a selected result if the $CO_2$ concentration measurement exceeds a given upper threshold value, the output being selected in accordance with a determination of which threshold value the $CO_2$ exceeds.

57. An apparatus as set forth in claim 54 further including a logic element (L1) coupled to said second comparing element (C1) for producing a predetermined selected output if the $CO_2$ concentration measurement exceeds the upper threshold value.

58. An apparatus as set forth in claim 45 or 47 further including means (E) for providing a variable threshold value for storage in said second memory means.

59. An apparatus as set forth in claim 45 or 47 further including a logic element (L1) coupled to said second comparing element (C1) for providing a predetermined, selected output, if the relationship of the $CO_2$ concentration measurement to the threshold value is such that the blood alcohol measurement is not an accurate indication of blood alcohol concentration.

60. An apparatus as set forth in claim 59 wherein said logic element provides a selected output comprising at least one of: producing an alarm, outputting a blood alcohol concentration value, not outputting blood alcohol concentration values, outputting measured $CO_2$ concentration properties, repeating the operation of the apparatus, and issuing instructions to an operator.

61. An apparatus as set forth in claim 45 or 47 wherein said apparatus further includes a calculating means (D) coupled to said sensing means and said output means for carrying out a calculation on the alcohol concentration measurement data to produce the blood alcohol concentration value.

62. An apparatus as set forth in claim 45 or 47 wherein said apparatus includes means for providing an indication of measured $CO_2$ concentration properties.

63. An apparatus as set forth in claim 45 or 47 wherein said sensor means is comprised of a pair of infrared sensors and associated band-pass filters for measuring the concentration of $CO_2$ and alcohol in the respiratory gases.

64. An apparatus as set forth in claim 45 or 47 wherein said sensor means comprising a single optical infrared sensor, a pair of band-pass filters, and control means for positioning one or the other of the band-pass filters in an infrared radiation path to said sensor to measure the concentration of $CO_2$ or alcohol in the respiratory gases.

65. An apparatus as set forth in claim 45 or 47 wherein said sensor means comprises two pairs of infrared radiation sources and infrared sensors, one of said pairs operating to measure the concentration $CO_2$, the other of said pairs operating to measure the concentration of alcohol.

* * * * *